//  // 
United States Patent [19]

Carson

[11] 4,277,684
[45] Jul. 7, 1981

[54] X-RAY COLLIMATOR, PARTICULARLY FOR USE IN COMPUTERIZED AXIAL TOMOGRAPHY APPARATUS

[75] Inventor: Arthur N. Carson, West Hartford, Conn.

[73] Assignee: U.S. Philips Corporation, New York, N.Y.

[21] Appl. No.: 825,590

[22] Filed: Aug. 18, 1977

[51] Int. Cl.³ ............................................ G01N 21/00
[52] U.S. Cl. ................................. 250/445 T; 250/513
[58] Field of Search ............... 250/505, 511, 512, 513, 250/445 T, 360, 571, 273

[56] References Cited

U.S. PATENT DOCUMENTS

| | | | |
|---|---|---|---|
| 2,492,031 | 12/1949 | Blatz ..................................... | 250/513 |
| 3,428,802 | 2/1969 | Mehta et al. .......................... | 250/273 |
| 4,066,901 | 1/1978 | Seppi et al. ......................... | 250/445 T |
| 4,096,389 | 6/1978 | Ashe et al. .......................... | 250/445 T |

*Primary Examiner*—Alfred E. Smith
*Assistant Examiner*—Thomas P. O'Hare
*Attorney, Agent, or Firm*—Thomas A. Briody; Robert T. Mayer; Jack E. Haken

[57] ABSTRACT

An X-ray collimator for use in computerized axial tomography apparatus includes a plurality of substantially parallel X-ray absorbing laminae disposed in the plane of a wedge-shaped X-ray beam. The length and position of each lamina with respect to a divergent X-ray source is chosen to maximize the ratio of X-ray flux impinging upon a detector array to flux falling within the collimator's penumbra, outside the detector array.

A single set of moveable jaws may be disposed at the collimator exit for adjustment of the beam thickness.

21 Claims, 4 Drawing Figures

X-RAY COLLIMATOR, PARTICULARLY FOR USE IN COMPUTERIZED AXIAL TOMOGRAPHY APPARATUS

This invention relates to X-ray collimators. More particularly, this invention relates to laminar X-ray collimation apparatus for producing wedge-shaped X-ray beams of adjustable thickness.

BACKGROUND OF THE INVENTION

Computerized apparatus for producing cross-section images of the body by the method of X-ray axial tomography are known, for example from U.S. Pat. Nos. 3,778,614 and 3,866,047 to Hounsfield. In one form of such apparatus a divergent beam of X-ray photons is directed from an X-ray source in a plane which passes through a body undergoing examination and thereafter impinges on an array of X-ray detectors which lie in the plane of examination. The X-ray source and detector array rotate (and in some embodiments also translate) about the body to produce a series of one-dimensional X-ray shadowgraphs which are combined in a digital computer, using well-known computational algorithms, to yield cross-section images of the examination plane.

Common X-ray sources, that is X-ray tube anodes or radioisotope sources, generally produce X-ray beams which diverge through substantial solid angles. In computerized axial tomography (CAT) equipment mechanical collimation is generally utilized in conjunction with the X-ray source to limit the divergence of the X-ray beam to a wedge or fan-shaped swath which is confined to the examination plane and to the included angle of the detector array. Unnecessary radiation dose to the patient and system noise from scattered X-ray photons is thereby reduced. The mechanical constraints of CAT equipment generally require that such X-ray source collimators have minimum weight, to permit rapid motion, and minimum length, to reduce the overall size of the rotating components and maximize the X-ray flux at the detector array.

Means are generally provided for adjusting the thickness of the X-ray beam, and thus the examination plane, in CAT apparatus. In prior art collimators, which generally comprised one or more long channels through bodies of X-ray absorbing material, two sets of moveable jaws were generally utilized to control the thickness of the X-ray swath. Such multiple jaw sets were required to limit the X-ray penumbra which would otherwise be produced if a single set of jaws were utilized with an X-ray source of finite dimensions.

SUMMARY OF THE INVENTION

An X-ray collimator for producing a planar, wedge-shaped swath of X-ray photons comprises a plurality of substantially parallel X-ray absorbing laminae disposed in the plane of the X-ray beam and spaced one from the other. The extent and relative displacement of the laminae along the X-ray beam as well as the number of such laminae are determined to individually maximize the ratio of X-ray flux within a defined beam thickness to X-ray flux outside the defined beam. X-ray photons at all points within the beam are generally confined to paths lying substantially parallel to the beam plane so that the beam thickness may be adjusted with a single set of moveable jaws with minimum X-ray flux in the penumbra. Collimators of the present invention are generally shorter and lighter than prior art, conventional collimators and are thus ideally suited for use in CAT scanning apparatus.

It is, therefore, an object of this invention to produce short, lightweight X-ray collimators for use in computerized axial tomography apparatus.

Another object of this invention is to allow adjustment of the thickness of a planar X-ray swath by means of a single set of moveable jaws.

BRIEF DESCRIPTION OF THE DRAWINGS

The novel features believed to be characteristic of the present invention are set forth in the appended claims. The invention itself, together with further objects and advantages thereof, may be best understood by reference to the following detailed descriptions, taken in connection with the appended drawings in which:

DESCRIPTION OF THE PREFERRED EMBODIMENTS

Figure 1:
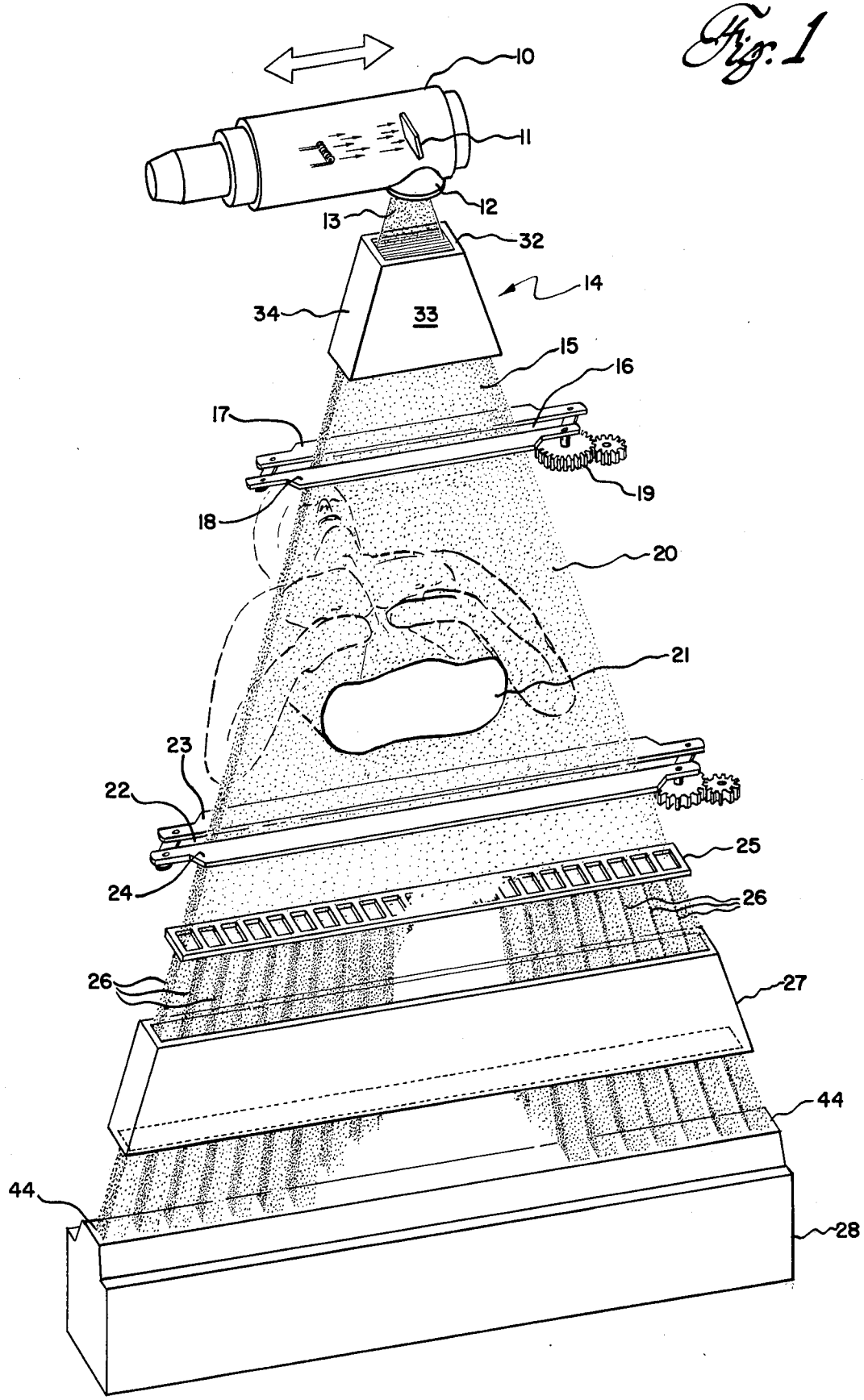
FIG. 1 schematically represents computerized axial tomography apparatus which includes collimating components of the present invention.

FIG. 1 is an X-ray measurement system of the present invention for use with computerized axial tomography apparatus. Electrons in an X-ray tube 10 impinge upon an anode 11 to produce a divergent X-ray beam 13 which emerges through a window 12. A collimator 14, more particularly described below, is disposed in the X-ray beam 13 to produce a planar, wedge-shaped exit beam 15. The thickness of the wedge-shaped beam 15 is determined by the overall internal thickness of the collimator 14. The collimator 14 further functions to confine photon propagation in the beam 15 to directions substantially parallel to the plane of the X-ray beam. The exit beam 15 then passes through a slot 16 between a set of parallel X-ray absorbing jaws 17 and 18 (which may comprise tungsten plates) which are adjustable via a gear drive 19 to produce a wedge-shaped X-ray beam 20 having an effective thickness determined by the width of the slot 16. The X-ray beam 20 is directed through a body 21 where it is selectively absorbed by tissues of varying density to produce a one-dimensional shadowgraph image of X-ray intensities. X-ray photons emerging from the body 21 pass through a slot 22 between a second set of parallel, X-ray absorbing jaws 23 and 24 which are adjusted by a gear mechanism to the same spacing as were the jaws 17 and 18. The jaws 23 and 24 function to absorb X-ray photons which are scattered by the body 21 or by other objects in the beam path and thus reduce noise in the X-ray measurement data.

The X-ray beam emerging from the slot 22 then passes through an X-ray absorbing aperture plate 25, where it is separated into beams 26 of equal cross section, width and angular spacing; which serves to define the spatial resolution of the measurement system. The individual beams 26 exiting the aperture plate 25 then pass through a detector collimator 27, which functions to reject scattered radiation, and impinge on an X-ray detector array 28 which may comprise scintillation crystals or any other type of radiation detectors which are commonly used in X-ray tomography apparatus.

Although any type of X-ray tube or other radiation source may be used, the tube 10 is most advantageously a lightweight X-ray tube having a fixed anode 11 which is disposed at an angle to both the electron beam and the perpendicular window 12 of the tube. The anode focal spot produced by an electron beam of generally circular cross section is thus projected as an ellipse in the plane of the window 13 and is ideally suited for producing a fan or wedge-shaped X-ray swath.

A beam path is defined by lines connecting points on the focal spot with points on the detector array. A central line connects the center of the focal spot (X-ray source) with the center of the detector array. Herein, and in the claims which follow, the length, extent, and position of the beam path and of associated structures are measured along lines which are parallel to the central line.

The source collimator 14 (FIGS. 1 and 2) comprises an open ended hollow housing shell 32 having side walls 33 which act as a baffle and are spaced to define the maximum thickness of the emergent X-ray beam 15 and divergent end walls 34 which serve to limit the divergence of the beam 15 to the width detector array 28. The housing shell 32 contains a plurality of substantially parallel, X-ray absorbing laminae 30 which are supported within the housing and spaced one from the other in a plurality of slots on the interior surface of the end walls 34. The length of each lamina 30 as well as its position within the housing and its spacing from adjacent laminae are fixed to maximize the ratio of X-ray flux emerging within the defined exit beam 15 to flux falling within a penumbra of that beam. This design is most effectively achieved with a digital computer following an iterative procedure which functions to maximize the ratio for each lamina.

Figure 3:
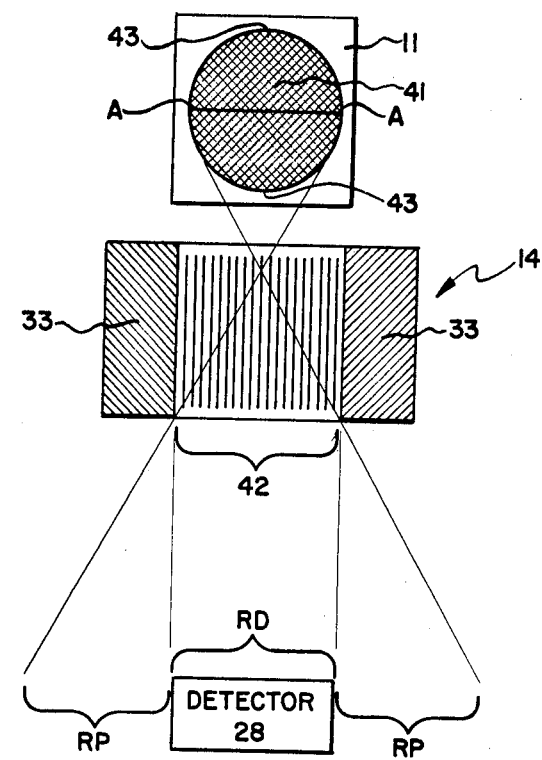
FIG. 3 illustrates the design of a collimator.

FIGS. 1 and 3 illustrate the design principles for the collimator 14. The width of the channel between the walls 34 of the collimator housing is found by connecting the outermost ends at each side of the focal spot 41 with the corresponding outermost ends 44 of the detector array 28; the position of the collimator 14 being fixed by such constraints as the dimensions of the X-ray tube window and available space in the scanning mechanism. The spacing between the laminae 30 is then assumed and the central line A—A of the focal spot is divided into a great number of equidistant points. Each point is assumed to radiate X-rays in all directions within the plane containing the central line of the focal spot and the detector. For each point the radiative flux RD reaching the detector is calculated. Then the flux RP in the penumbra (i.e. the flux passing through the collimator but not reaching the detector) is also calculated.

$$R = \frac{\sum_{n=0}^{N} RD}{\sum_{n=0}^{N} RP}$$

is maximized by selecting values for the length and position of each lamina.

As an example, collimators having equally spaced, symetrically disposed laminae were optimally designed for a system wherein the beam originated at a 15 mm thick focal spot and terminated at a 20 mm thick detector array approximately 1.2 meters from the focal spot. The collimator lay between 59.5 and 139.7 millimeters from the focal spot. Table I summarizes the calculated performance of collimators containing various numbers of laminae as compared to a conventional collimator with the same exterior dimensions.

TABLE I

| Number of Laminae | % RD | % RP | RD/RP / (RD/RP)$_o$ |
|---|---|---|---|
| 0 | 100% | 100% | 1 |
| 5 | 89% | 29% | 3.01X |
| 9 | 73% | 10% | 7.05X |
| 13 | 70% | 4.1% | 17.29X |
| 17 | 61% | 3.8% | 16.1X |
| 21 | 55% | 0.9% | 62X |

In all cases the laminae 30 comprised 0.1 mm depleted uranium foil. Tungsten laminae are also suitable and allow less expensive fabrication. The collimator housing may, for example, comprise brass plate. A Fortran language computer program which is useful for calculating laminae configurations is set forth in Appendix A to enable others to more easily practice the invention.

Figure 2:
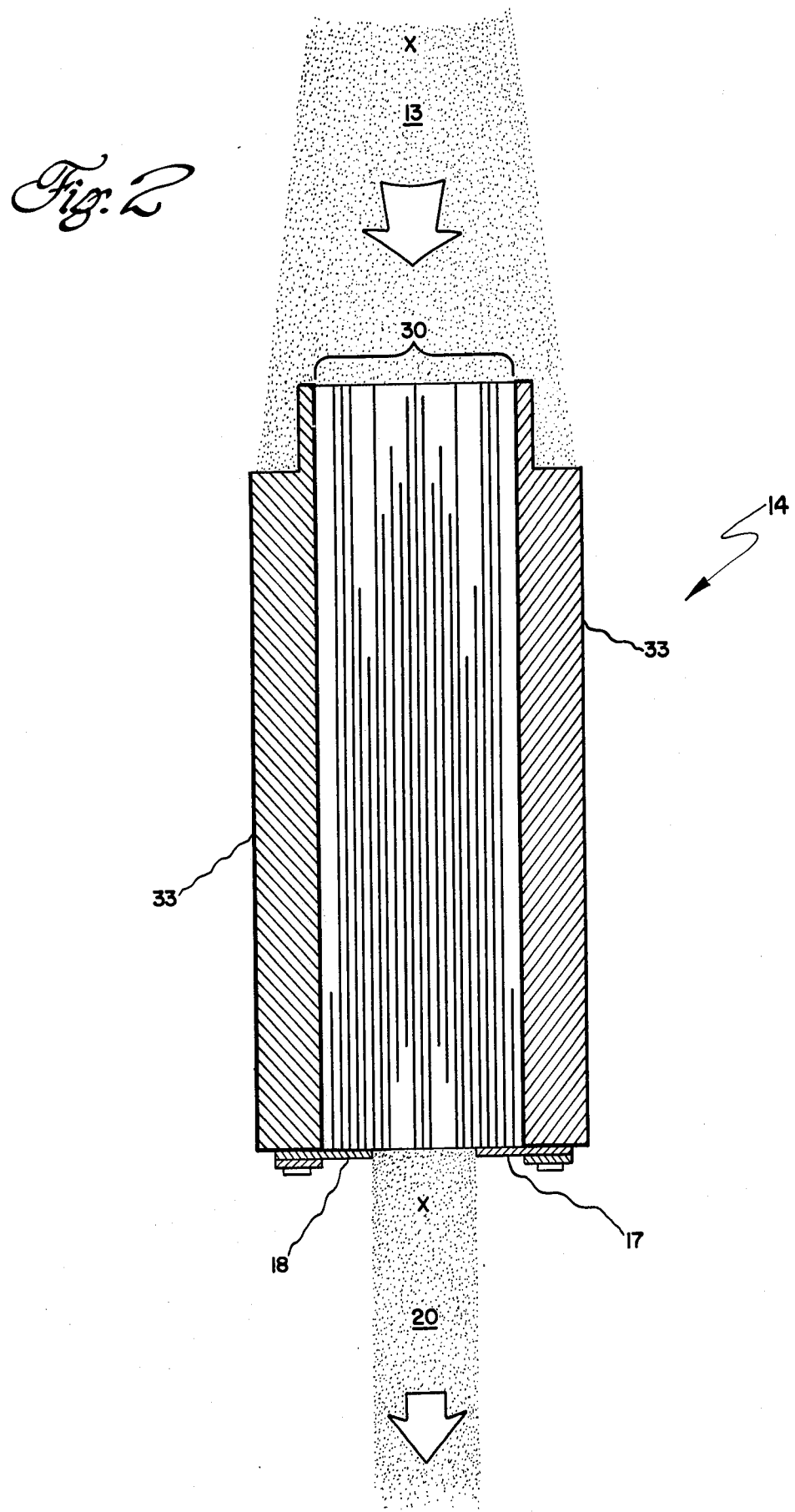
FIG. 2 is a sectional view of a laminar collimator of the present invention.
Figure 4:
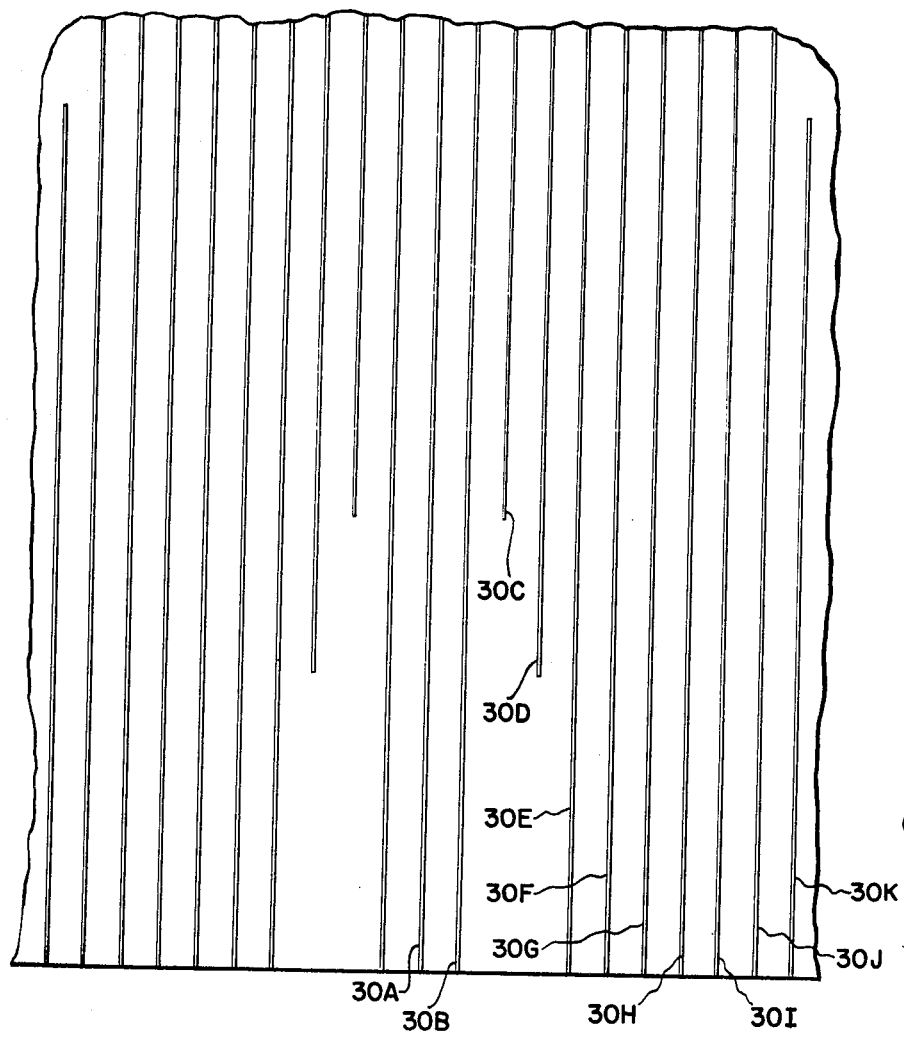
FIG. 4 is an enlarged sectional view of a portion of the collimator of FIG. 2 illustrating the distribution of laminae therein.

FIG. 4 is an enlarged section of a collimator of FIG. 2 showing the spacing and extent of the laminae 30A–30K. By way of example Table II sets forth the spacing X, the distance between the lower end of the lamina and the housing 32 exit end, $Y_1$, and the distance between the top of the lamina and the housing exit end $Y_2$, for an optimal collimator comprising 21 equally spaced laminae for the source and detector spacing above which produces a convergent beam from a 15 mm focal spot to an 8 mm detector.

TABLE II

| Lamina # | X(in) | $Y_1$(in) | $Y_2$(in) |
|---|---|---|---|
| 30A | 0 | 0 | 2.955 |
| 30B | .03 | 0 | 2.898 |
| 30C | .06 | 0.242 | 2.159 |
| 30D | .09 | 0.109 | 2.458 |
| 30E | .12 | 0.00 | 2.955 |
| 30F | .15 | 0.00 | 1.902 |
| 30G | .18 | 0.00 | 2.167 |
| 30H | .21 | 0.00 | 2.955 |
| 30I | .24 | 0.00 | 2.955 |
| 30J | .27 | 0.00 | 2.898 |
| 30K | .30 | 0.00 | 0.606 |

The present invention provides a low weight, short structure producing a wedge-shaped planar swath of X-rays used in computerized axial tomography apparatus. X-ray photon flux in the beam emerging from the collimator is substantially parallel to the X-ray beam plane so that beam thickness may be effectively controlled with a single set of moveable jaws and minimal penumbra effects.

The invention has been described in detail herein in accord with certain embodiments thereof, yet many modifications and changes therein may be effected by those skilled in the art.

Accordingly, it is intended by the appended claims to cover all such modifications and changes as fall within the true spirit and scope of the invention.

APPENDIX A

```
0001        REAL HM(21),GM(21)
0002        REAL PHM1(21,16),PHM2(21,16)
0003        REAL AD(3),AT(2)
0004        COMMON /A/AL2(16),AL3(16),PH1(21,16),PH2(21,16),H(21),G(21)
0005        COMMON /B/RP,RPO,RD,RDO
0006        COMMON /C/HMX(21),GMX(21),PHMX1(21,16),PHMX2(21,16)
0007        COMMON /D/DE,TO,RMX,RDMX,RPMX,DHP,N,HCL,X7,X4,H3
0008        COMMON /E/X(16),DI(21),AL1(16),AL4(16),IM,I,H2,KM
0009        DATA DH,DG,H1,H2,H3/3.375,3.375,59.5,139.7,1193.8/
0010        DATA HCL,XCL,X4,X8/444.5,0.430835,-7.5,10./
0011        DATA KM,LMX,IM,K/16,5,1,1/
0012        X6=(H1*XCL-X4*(HCL-H1))/HCL
0013        X7=(H2*XCL-X4*(HCL-H2))/HCL
0014        XS=(XCL*H3-X8*HCL)/(H3-HCL)
0015        X3=-X6
0016        X2=-X7
0017        X1=-X3
0018        X(1)=X4
0019  100   AL1(K)=ATAN2((X7-X(K)),H2)
0020        AL2(K)=ATAN2((X3-X(K)),H3)
0021        IF(X(K).GT.XS)AL2(K)=ATAN2((XCL-X(K)),HCL)
0023        AL4(K)=ATAN2((X2-X(K)),H2)
0024        AL3(K)=ATAN2((X1-X(K)),H3)
0025        IF(X(K).LT.-XS)AL3(K)=ATAN2((-XCL-X(K)),HCL)
0027        RPO=RPO+AL1(K)-AL2(K)+AL3(K)-AL4(K)
0028        RDO=RDO+AL2(K)-AL3(K)
0029        K=K+1
0030        X(K)=X(K-1)-2.*X4/15.
0031        IF(K.LE.KM)GOTO100
0033        R=RDO/RPO
0034        CALL DATE(AD)
0035        CALL TIME(AT)
0036        WRITE(6,104)(AD(I),I=1,3),(AT(I),I=1,2)
0037  104   FORMAT(14H1COLLIMATOR    3A4,3X,2A4//)
0038        WRITE(6,105)(AL1(K),AL2(K),AL3(K),AL4(K),K=1,KM),R,RDO,RPO
0039  105   FORMAT(16(1H 7X,4F11.7/)/1H 7X,3F11.7)
0040        TO=SECNDS(1.0)
0041        GOTO650
0042  345   CALL S1
0043  350   R=RD/RP
0044        IF(R.LE.RD)GOTO370
0046        RH=R
0047        RDM=RD
0048        RPH=RP
0049        DO356 L=1,IM
0050        HM(L)=H(L)
0051        GM(L)=G(L)
0052        DO355 K=1,KM
0053        PHM1(L,K)=PH1(L,K)
0054  355   PHM2(L,K)=PH2(L,K)
0055  356   CONTINUE
0056  370   IF(G(I)+DG.GT.H2-H1-H(I))GOTO380
0058        G(I)=G(I)+DG
0059        IF(H(I).EQ.0.)G(I)=0.
0061        H(I+1)=H(I)
0062        G(I+1)=G(I)
0063        IF(H(I).EQ.0.)GOTO380
0065        GOTO345
0066  380   DO386 L=I,I+1
0067        H(L)=HM(L)
0068        G(L)=GM(L)
0069        DO385 K=1,KM
0070        PH1(L,K)=PHM1(L,K)
0071  385   PH2(L,K)=PHM2(L,K)
0072  386   CONTINUE
```

```
0073            N=N+1
0074            IF(RM.LE.RMX)GOTO603
0076            RMX=RM
0077            RDMX=RDM
0078            RPMX=RPM
0079            DO450 L=1,IM
0080            HMX(L)=HM(L)
0081            GMX(L)=GM(L)
0082            DO425 K=1,KM
0083            PHMX1(L,K)=PHM1(L,K)
0084      425   PHMX2(L,K)=PHM2(L,K)
0085      450   CONTINUE
0086      603   IF(RM.LT.RMO)DHP=-DHP/2.
0088            IF(RM.NE.RMO)GOTO605
0090            IF(NP.GT.1)GOTO620
0092            NP=NP+1
0093      605   IF(H(I)+DHP.GE.H2-H1)DHP=+ABS(DHP)/2.
0095            RMO=RM
0096            IF(H(I)+DHP.LE.0.)DHP=-ABS(DHP)/2.
0098            IF(H(I)+DHP.LT.0.OR.H(I)+DHP.GT.H2-H1)GOTO605
0100            IF(ABS(DHP).LT.0.5)GOTO620
0102      610   H(I)=H(I)+DHP
0103            G(I)=-DG
0104            GOTO370
0105      620   DHP=DH
0106            NP=0
0107            RM=0.
0108            I=I+2
0109            H(I)=0.
0110            IF(I+1.LE.IM)GOTO610
0112            NN=NN+1
0113            I=0
0114            IF(NN.LE.2)GOTO620
0116            NN=0
0117            CALL S2
0118            IF(IM.EQ.IMX)GOTO900
0120      650   IM=IM+4
0121            RMX=0.
0122            RMO=0.
0123            RM=0.
0124            DDI=2.*(AMIN1(X7,X6))/(IM-1)
0125            DI(1)=0.
0126            H(1)=H2-H1
0127            I=2
0128            DHP=DH
0129            GOTO670
0130      660   DO800    I=3,IM,2
0131            DI(I)=DI(I-2)+DDI
0132            DI(I-1)=-DI(I)
0133            H(I)=0.
0134            H(I-1)=H(I)
0135            G(I)=0.
0136            G(I-1)=G(I)
0137      670   DO700 K=1,KM
0138            PH1(I,K)=ATAN2((DI(I)-X(K)),(H2-G(I)-H(I)))
0139            PH1(I-1,K)=ATAN2((DI(I-1)-X(K)),(H2-G(I-1)-H(I-1)))
0140            PH2(I,K)=ATAN2((DI(I)-X(K)),(H2-G(I)))
0141      700   PH2(I-1,K)=ATAN2((DI(I-1)-X(K)),(H2-G(I-1)))
0142            IF(I.EQ.2)GOTO660
0144      800   CONTINUE
0145            I=2
0146            GOTO345
0147      900   CALL PATE(AD)
0148            CALL TIME(AT)
0149            WRITE(6,904)(AD(I),I=1,3),(AT(I),I=1,2)
0150      904   FORMAT(/3X,3A4,3X,2A4)
0151            STOP
0152            END
```

```
0001           SUBROUTINE S1
0002           REAL W1(21,2),W2(21,2),B(2,21)
0003           REAL C(2,21),D(2,21),E(2,21)
0004           COMMON /A/AL2(16),AL3(16),PH1(21,16),PH2(21,16),H(21),G(21)
0005           COMMON /B/RP,RPO,RD,RDO
0006           COMMON /E/X(16),DI(21),AL1(16),AL4(16),IM,I,H2,KM
0007   160     K=1
0008           RP=RPO
0009           RD=RDO
0010   170     L=0
0011           L1=0
0012           L2=0
0013   180     IF(L.EQ.IM)GOTO190
0015           L=L+1
0016           IF(L.LT.I.OR.L.GT.I+1)GOTO182
0018           PH1(L,K)=ATAN2((DI(L)-X(K)),(H2-G(L)-H(L)))
0019           PH2(L,K)=ATAN2((DI(L)-X(K)),(H2-G(L)))
0020   182     IF(PH1(L,K).EQ.PH2(L,K))GOTO180
0022           IF(PH1(L,K).GT.0.)GOTO200
0024           L2=L2+1
0025           W1(L2,2)=ABS(PH1(L,K))
0026           W2(L2,2)=ABS(PH2(L,K))
0027           GOTO180
0028   200     L1=L1+1
0029           W1(L1,1)=PH1(L,K)
0030           W2(L1,1)=PH2(L,K)
0031           GOTO180
0032   190     M=0
0033           JF=L1
0034           NU=1
0035           A1=1.570795
0036   210     IF(M.EQ.JF)GOTO220
0038           L=0
0039   230     IF(L.EQ.JF)GOTO240
0041           L=L+1
0042           IF(W1(L,NU).GT.A1)GOTO230
0044           IF(M.EQ.0)GOTO250
0046           IF(W1(L,NU).LE.B(NU,M))GOTO230
0048   250     A1=W1(L,NU)
0049           A2=W2(L,NU)
0050           GOTO230
0051   240     M=M+1
0052           B(NU,M)=A1
0053           C(NU,M)=A2
0054           A1=1.570795
0055           GOTO210
0056   220     IF(NU.EQ.2)GOTO260
0058           M=0
0059           NU=2
0060           JF=L2
0061           A1=1.570795
0062           L=0
0063           IF(L2.EQ.0)GOTO280
0065           GOTO210
0066   260     M=JF
0067           L=1
0068   265     D(NU,L)=B(NU,M)
0069           E(NU,L)=C(NU,M)
0070   270     IF(M.EQ.1)GOTO280
0072           M=M-1
0073           IF(B(NU,M).GE.E(NU,L))GOTO275
0075           L=L+1
0076           GOTO265
0077   275     IF(C(NU,M).LT.E(NU,L))E(NU,L)=C(NU,M)
0079           GOTO270
0080   280     IF(NU.EQ.1)GOTO300
0082           NU=1
0083           JF=L1
0084           M2=L
0085           IF(L1.NE.0)GOTO260
0087           L=0
0088   300     M=0
0089   310     IF(M.EQ.L)GOTO335
```

```
0091            N=M+1
0092            B(NU,M)=-E(NU,M)
0093            IF(NU.EQ.1)B(NU,M)=D(NU,M)
0095            C(NU,M)=-D(NU,M)
0096            IF(NU.EQ.1)C(NU,M)=E(NU,M)
0098            P=C(NU,M)
0099            IF(P.LT.AL2(K))GOTO320
0101            IF(P.GE.AL1(K))GOTO310
0103    315     Q=AMIN1(AL1(K),B(NU,M))
0104            RP=RP-(Q-P)
0105            GOTO310
0106    320     IF(C(NU,M).LT.AL3(K))GOTO330
0108    325     Q=AMIN1(AL2(K),B(NU,M))
0109            RD=RD-(Q-P)
0110            P=AL2(K)
0111            IF(B(NU,M).LT.AL2(K))GOTO310
0113            GOTO315
0114    330     P=AMAX1(AL4(K),C(NU,M))
0115            Q=AMIN1(AL3(K),B(NU,M))
0116            RP=RP-(Q-P)
0117            P=AL3(K)
0118            IF(B(NU,M).LT.P)GOTO310
0120            GOTO325
0121    335     IF(NU.NE.1)GOTO340
0123            NU=2
0124            L=M2
0125            M=0
0126            GOTO310
0127    340     IF(K.EQ.KM)RETURN
0129            K=K+1
0130            GOTO170
0131            END
0001            SUBROUTINE S2
0002            INTEGER IV(202)
0003            COMMON /C/HMX(21),CMX(21),PHMX1(21,16),PHMX2(21,16)
0004            COMMON /D/DE,T0,RMX,RDMX,RPMX,DHP,N,HCL,X7,X4,H3
0005            COMMON /E/X(16),DI(21),AL1(16),AL4(16),IM,I,H2,KM
0006    600     FORMAT(//6F12.3/(6F12.3))
0007    601     FORMAT(3F12.3,3I12)
0008    602     FORMAT(//2F12.3/(32I4))
0009            DE=(SECNDS(1.0)-T0)/60.
0010            T0=SECNDS(1.0)
0011            WRITE(6,600)RMX,RDMX,RPMX,(HMX(L),CMX(L),DI(L),L=1,IM)
0012            WRITE(6,601)DE,DHP,RMX,IM,I,N
0013            U=HCL
0014            DO648 L=1,2
0015            XL=(X7-X4)/H2*U+X4
0016            XY=-1.01*XL
0017            DO646 J=1,201
0018            IV(J)=0
0019            XY=XY+XL/100.
0020            DO644 K=1,KM
0021            ANG=ATAN2((XY-X(K)),U)
0022            IF(ANG.GT.AL1(K).OR.ANG.LT.AL4(K))GOTO644
0024            DO642 I=1,IM
0025            IF(ABS(ANG).LT.ABS(PHMX2(I,K)))GOTO642
0027            IF(ABS(ANG).GT.ABS(PHMX1(I,K)))GOTO642
0029            IF(ANG*PHMX1(I,K).GT.0.)GOTO644
0031    642     CONTINUE
0032            IV(J)=IV(J)+1
0033    644     CONTINUE
0034    646     CONTINUE
0035            WRITE(6,602)U,XL,(IV(J),J=1,201)
0036    648     U=H3
0037            RETURN
0038            END
```

What is claimed is:

1. A collimator for accepting a divergent input beam from a radiation source and for producing therefrom a thick, substantially planar swath of radiation which impinges upon an array of radiation detectors; a central ine connecting the center of the source to the center of the array and a beam path being defined by all points which lie on lines connecting points on said source to points on said array, comprising:

baffle means, surrounding a limited portion of said beam path and defining a central perforation on said path, which function to absorb radiation propagating outside of said path; and a plurality of planar, radiation-absorbing laminae, disposed within said perforation substantially parallel to the plane of said swath, the extent of ones of said laminae, measured along lines which are parallel to said central ray, being different than the extent of others of said laminae.

2. The collimator of claim 1 wherein the distance, measured along lines which are parallel to said central ray, from ones of said laminae to said source is different than the distance, measured along lines which are parallel to said central ray, from others of said laminae to said source.

3. The collimator of claim 2, wherein the position and extent of said laminae along said path maximizes the ratio of the radiation flux impinging on said detector array to the radiation flux within a penumbra of said baffle means.

4. The collimator of claim 3, wherein said laminae are equally spaced, one from another.

5. The collimator of claim 3, wherein said laminae comprise tungsten sheets.

6. The collimator of claim 3, wherein said laminae comprise uranium sheets.

7. Measurement apparatus for X-ray computerized axial tomography comprising, in combination:
   a source of divergent X-ray radiation having a finite thickness;
   an array of radiation detectors disposed to accept radiation in a substantially planar swath from said source, a beam path being defined by lines connecting points on said source with points on said array;
   baffle means surrounding said beam path, along a limited portion of its length, having a perforation therein, which function to absorb radiation from said source which propagates outside the beam path;
   a plurality of planar radiation-absorbing laminae disposed in said perforation substantially parallel to the plane of said swath and spaced one from another;
   one pair of movable jaw means defining an elongate radiation transmitting slot therebetween, disposed across said swath parallel to said laminae and between said laminae and said array, which function to absorb radiation propagating outside said slot and thereby determine the thickness of said swath at said array;
   means for moving said jaw means to adjust the thickness of said slot; and
   wherein the extent of ones of said laminae along said beam path is different than the extent of others of said laminae along said beam path.

8. Measurement apparatus for X-ray computerized axial tomography comprising, in combination:
   a source of divergent X-ray radiation having a finite thickness;
   an array of radiation detectors disposed to accept radiation in a substantially planar swath from said source, a beam path being defined by lines connecting points on said source with points on said array;
   baffle means surrounding said beam path, along a limited portion of its length, having a perforation therein, which function to absorb radiation from said source which propagates outside the beam path;
   a plurality of planar radiation-absorbing laminae disposed in said perforation substantially parallel to the plane of said swath and spaced one from another;
   one pair of movable jaw means defining an elongate radiation transmitting slot therebetween, disposed across said swath parallel to said laminae and between said laminae and said array, which function to absorb radiation propagating outside said slot and thereby determine the thickness of said swath at said array;
   means for moving said jaw means to adjust the thickness of said slot; and
   wherein the distance from ones of said laminae to said source is different than the distance from others of said laminae to said source.

9. Apparatus of claim 7 wherein the distance from ones of said laminae to said source is different than the distance from others of said laminae to said source.

10. Apparatus for producing a substantially planar swath of X-ray radiation, having adjustable thickness, along the width of a radiation detector array; comprising, in combination:
    a radiation source, a beam path being defined by lines connecting points on said source with points on said detector array;
    baffle means surrounding a limited portion of said path and defining a perforation thereon, which function to absorb radiation progagating outside the path;
    a plurality of planar radiation-absorbing laminae disposed within said perforation substantially parallel to the plane of said swath;
    one pair of radiation absorbing jaws disposed between said laminae and said detector array which define an elongated slot parallel to said detector array and within said beam path; means for moving said jaws to adjust the thickness of said slot; and
    wherein the extent of ones of said laminae along said beam path is different than the extent of others of said laminae along said beam path.

11. Apparatus for producing a substantially planar swath of X-ray radiation, having adjustable thickness, along the width of a radiation detector array; comprising, in combination:
    a radiation source, a beam path being defined by lines connecting points on said source with points on said detector array;
    baffle means surrounding a limited portion of said path and defining a perforation thereon, which function to absorb radiation progagating outside the path;
    a plurality of planar radiation-absorbing laminae disposed within said perforation substantially parallel to the plane of said swath;
    one pair of radiation absorbing jaws disposed between said laminae and said detector array which define an elongated slot parallel to said detector array and within said beam path;
    means for moving said jaws to adjust the thickness of said slot; and
    wherein the distance from ones of said laminae to said source is different than the distance from others of said laminae to said source.

12. Apparatus of claim 10 wherein the distance from ones of said laminae to said source is different than the distance from others of said laminae to said source.

13. The apparatus of claim 12, wherein the position and extent of each lamina, along said path, maximizes the ratio of the radiation flux impinging on said detector array to the radiation flux within a penumbra of said baffle means.

14. The apparatus of claim 13, wherein said laminae are equally spaced, one from another.

15. The apparatus of claim 9, wherein the position and extent of each of said laminae along said beam path maximizes the ratio of the X-ray flux impinging on said detector array to the X-ray flux in a penumbra of said baffle means.

16. The apparatus of claim 15, wherein said laminae are equally spaced, one from another.

17. The apparatus of claim 15, wherein said laminae comprise tungsten.

18. The apparatus of claim 15, wherein said laminae comprise uranium.

19. The apparatus of claim 15, wherein said baffle means comprise a brass housing which supports said laminae.

20. The apparatus of claim 15, wherein said jaw means comprise tungsten plates.

21. A collimator for accepting a divergent input beam from a radiation source and for producing therefrom a thick, substantially planar swath of radiation which impinges upon an array of radiation detectors; a central ray connecting the center of the source to the center of the array and a beam path being defined by all points which lie on lines connecting points on said source to points on said array, comprising:

baffle means, surrounding a limited portion of said beam path and defining a central perforation on said path, which function to absorb radiation propagating outside of said path; and a plurality of planar, radiation-absorbing laminae, disposed within said perforation substantially parallel to the plane of said swath, the distance, measured along lines which are parallel to said central ray, from ones of said laminae to said source being different than the distance, measured along lines which are parallel to said central ray, from others of said laminae to said source.

* * * * *